(12) United States Patent
Kam

(10) Patent No.: US 7,225,172 B2
(45) Date of Patent: May 29, 2007

(54) METHOD AND APPARATUS FOR MULTIVARIABLE ANALYSIS OF BIOLOGICAL MEASUREMENTS

(75) Inventor: Zvi Kam, Tel Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 771 days.

(21) Appl. No.: 10/304,551

(22) Filed: Nov. 26, 2002

(65) Prior Publication Data

US 2003/0158829 A1    Aug. 21, 2003

Related U.S. Application Data

(63) Continuation-in-part of application No. 09/345,746, filed on Jul. 1, 1999, now abandoned.

(51) Int. Cl.
| | |
|---|---|
| *G06E 1/00* | (2006.01) |
| *G06E 3/00* | (2006.01) |
| *G06F 15/18* | (2006.01) |
| *G06G 7/00* | (2006.01) |
| *G06N 3/02* | (2006.01) |

(52) U.S. Cl. .......................... 706/15; 706/16; 706/924
(58) Field of Classification Search ................ 706/15, 706/16, 924; 364/578; 707/100
See application file for complete search history.

(56) References Cited

U.S. PATENT DOCUMENTS

| | | | | |
|---|---|---|---|---|
| 5,777,888 A | * | 7/1998 | Rine et al. .................... | 702/19 |
| 5,980,096 A | * | 11/1999 | Thalhammer-Reyero .... | 707/100 |
| 6,038,338 A | * | 3/2000 | Nguyen ....................... | 382/159 |
| 6,295,514 B1 | * | 9/2001 | Agrafiotis et al. ............ | 703/12 |

OTHER PUBLICATIONS

Bernard Widrow, 30 Years of Adaptive Neural Networks: Perceptron, Madaline, and Backpropagation, Sep. 1990, IEEE, 1415-1442.*
Vasile Palade, Genetic Algorithm Optimization of Knowledge Extraction from Neural Networks, 1999, IEEE, 752-758.*
BrainMaker Professional, Jul. 1993, 7-10, 7-11, 10-41.*

* cited by examiner

*Primary Examiner*—Joseph P. Hirl
(74) *Attorney, Agent, or Firm*—Martin Fleit; Paul D. Bianco; Fleit Kain Gibbons Gutman Bongini & Bianco P.L.

(57) ABSTRACT

In a method and apparatus for analyzing multivariable data sets, a general computerized platform is provided for evaluating the relationship between large number of measurements of sets of variables characterizing components of complex states of a system under induced stimulation or controlled conditions. The linked responses of variables and their temporal relations tell about the network of interactions and their hierarchy. Processing of data sets by a simple neural network gives a matrix of weight parameters, that allow to identify fingerprints of complex states characterized by patterns of measured variable and estimate the interactions between the components characterized by the measured variables. The results are provided numerically and by color-coded presentation indicating dominating relations between variables and strongly responding variables. When applied to dynamic responses of a system, the analysis can construct a schematic hierarchical architecture of the network of interaction between the components of the studied system. Applications in biology include analysis of measurements characterizing responses of molecular components in cells under changes induced by stimuli (e.g. drugs, growth factors, hormones, mutations or forced expression of a proteins), and identification of complex cellular states (e.g. proliferation, differentiation, transformation, starvation, necrosis, apoptosis, and the time dependencies of the above effects).

12 Claims, 12 Drawing Sheets

BLOCK DIAGRAM

TIME DEPENDENCE TRANSIENT     a>b>c>d>e

| | | | | | | | | | | |
|---|---|---|---|---|---|---|---|---|---|---|
| 1=0 | | | | | A | 1=t | | | | |
| t | 1=0 | | | | B | t | 1=t | | | |
| | t | 1=t | | | C | | t | 1=t | | |
| | | t | 1=0 | | D | | | t | 1=t | |
| | | | t | 1=t | E | | | | t | 1=t |
| A | B | C | D | E | | T2 | T3 | T4 | T5 | T6 |
| 1 | | | | | T1 | | | | | |
| | 1 | | | | T2 | | | | | |
| | | 1 | | | T3 | | | | | |
| | | | 1 | | T4 | | | | | |
| | | | | 1 | T5 | | | | | |

FIG. 2F

TIME DEPENDENCE SUSTAINED     a>b>c>d>e

| | | | | | | | | | | |
|---|---|---|---|---|---|---|---|---|---|---|
| 1 | | | | | A | 1 | | | | |
| 1 | 1 | | | | B | 1 | 1 | | | |
| 1 | 1 | 1 | | | C | 1 | 1 | 1 | | |
| 1 | 1 | 1 | 1 | | D | 1 | 1 | 1 | 1 | |
| 1 | 1 | 1 | 1 | 1 | E | 1 | 1 | 1 | 1 | 1 |
| A | B | C | D | E | | T2 | T3 | T4 | T5 | T6 |
| 1 | | | | | T1 | | | | | |
| | 1 | | | | T2 | | | | | |
| | | 1 | | | T3 | | | | | |
| | | | 1 | | T4 | | | | | |
| | | | | 1 | T5 | | | | | |

FIG. 2G

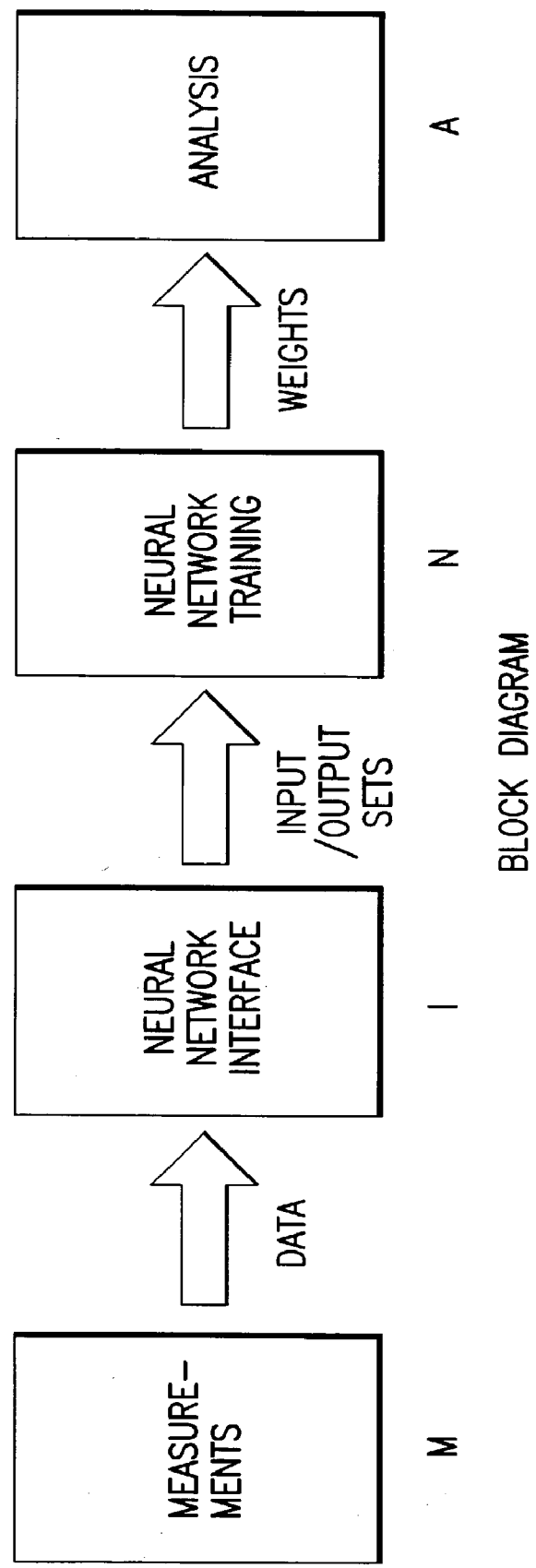

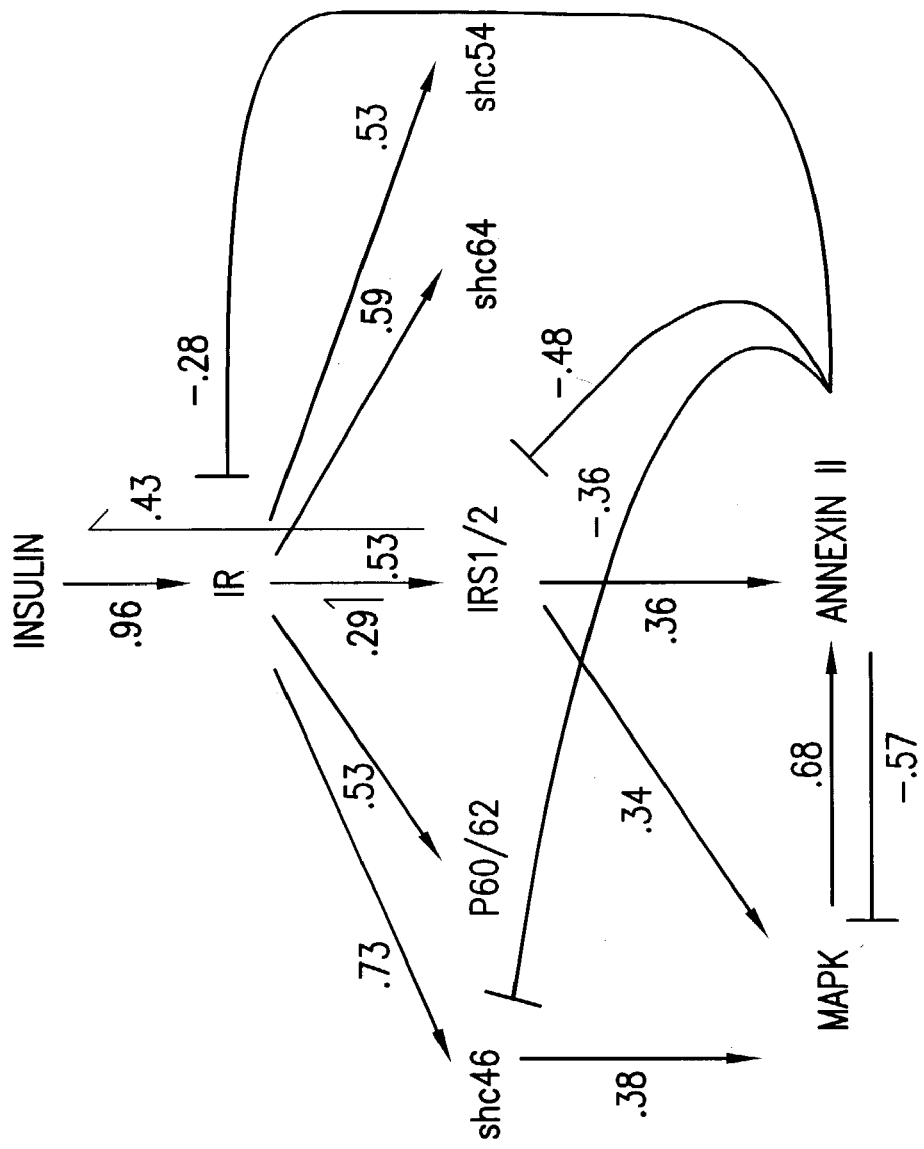
FIG. 7B THE INSULIN PATHWAY

METHOD AND APPARATUS FOR MULTIVARIABLE ANALYSIS OF BIOLOGICAL MEASUREMENTS

RELATED CASES

This application is a continuation-in-part of application Ser. No. 09/345,746 filed Jul. 1, 1999 now abandoned.

BACKGROUND OF THE INVENTION

1. Field of the Invention

The present invention relates to a method and apparatus for analyzing multivariable experimental data, and for drawing conclusions concerning relationships between these variables. The invention is especially useful for analyzing processes in complex systems consisting of many components, such as in biology, where the experimentally derived data sets characterize these components and the inducing and inhibiting interactions between them.

2. Prior Art

Modern biological research is revealing in growing details the complexity of living systems. Thus it is generally appreciated that biological mechanisms are the outcome of a large number of highly interactive molecular events. Experimental techniques must provide therefore not only increased sensitivity and selectivity to minute (even individual) molecular components, but also characterize the whole biological context, by simultaneous measuring of many variables at each single experimental procedure, reporting about as many relevant components participating in the studied process.

Biological systems can be described at various levels and resolutions. Modern biology describes biological processes in terms of molecular components. Molecular mechanisms are typically described as pathways consisting of sets of rules for the way molecules interact, reacting to each other, and changing properties to inhibit or induce their functional activity in response to a stimulus. As a result of these sets of rules many changes are induces, leading to a new cellular state (e.g. enter a proliferative cell cycle). This process is often termed a cellular decision mechanism or a signaling pathway. Molecular mechanisms are often presented graphically as a set of nodes connected by a network of line segments, where the nodes are usually the molecular components and the lines between them present the interactions. A molecule suspected to be involved in a process help explore its mechanisms by introducing changes in its activity and searching for correlated changes induced on other molecules.

Exhaustive exploration of biological systems is the goal of present efforts to develop automated large scale assays such as multisensor arrays and DNA chips, in order to document the expression patterns of genes. One of the most commonly used techniques in biology, namely polyacrilamide gel electrophoresis (PAGE), also provide information about the protein inventory of cells and tissues by quantifying tens (in one dimensional gels) to hundreds of bands (in two dimensional gels). Comparison of electrophoretic patterns following specific treatments can reveal multiple changes in the levels of many protein bands. Moreover, combined with immunoblotting techniques, such changes can be assigned to specific proteins and their post-translational modifications and activation. However, these changes are usually too numerous to reveal, or even suggest definitive causal relationships between individual molecular components. This can be studied by quantitative analysis methods, such as this invention.

An example to illustrate the information extractable by quantitative analysis of biological measurements is signal transduction in cells. Signal transduction mechanisms have logical structure of well defined input stimulants, and they lend themselves experimentally to multivariable measurements of cell output responses, for example by recording the many activated molecular components by phosphorylation changes, using phosphotyrosine gel blots.

Understanding of the molecular mechanisms underlying signal transduction in cells has advanced greatly in recent years, and include activation, alteration, regulation, maintenance and termination of various cellular functions [Alberts et al. 1994]. Classically, signaling pathways were described as cascades of sequentially activated events leading to recognizable responses. Responses at cellular levels involve post-translational modifications of proteins (like phosphorylation or dephosphorylation) affecting molecular interactions and enzymatic activities, causing translocations between different cell compartments, notably between the nucleus and the cytoplasm, and leading to changes in the expression of genes and global alterations in morphology and in cell cycle. Due to the multitude of processes involved (directly or indirectly), characterization of the molecular mechanisms induced by cell stimulation is based on a wide variety of immunological, biochemical, genetic and cell biological approaches.

Genetic manipulations are undoubtedly the most powerful method to dissect molecular mechanisms. Many genetic manipulations are binary (yes/no, such as forced expression in transgenic cells and animals or knockouts). This makes them ideally suited to assign the function of specific molecules in signaling cascades, and identify the downstream events. Yet, assigning attributes to molecular changes like cause and effect (upstream-downstream relationships) which appear often obvious in model systems, becomes difficult in many realistic conditions. Isolation of homologous molecules in various species, ranging from bacteria and yeast to mammals, indicates the universality of signal transduction genes. However, their detailed functionality often displays system dependent quantitative as well as qualitative diversion compared to their characterization in specialized systems (such as low forms of life or overexpressing cell lines). The increasing complexity in species with larger genome is therefore not only attributed to the increasing number of independent cascade-like pathways, but also on the multiplicity of cross-talks and interactions between pathways, which turn them into interlinked networks. This network architecture is believed to account for the robustness of higher species against random mutations, without compromising the evolutionary potential: duplication of pathways gave rise to networks of cross-talking components, and independent mutations evolved abilities to respond specifically and non-linearly to a growing repertoire of stimuli in a cell-type dependent manner [Bray 1990]. There are though special, and extremely important cases of degenerate network architectures. In order to guarantee synchrony of cellular functions (for example, cell cycle progression) cells evolved mechanisms that cumulate information about multiple conditions before deciding to act, which then spreads out signals to many responses. It is this reduced robustness of the critical locales of cellular decision nodes (or checkpoints) that is associated with cancer [Fearon and Vogelstein, 1990]. Characterizing the hierarchy of interactions between the components in signaling pathway networks and identifying the logical architecture of cellular decision making is therefore a critical question that draws intensive research efforts.

How is it possible to probe a network architecture such as that underlying cell signaling pathways? The problem of defining the content of an electronic black box by stimulating its inputs and measuring the signals emerging at the outputs has been formulated for a network of linear elements long time ago. The dynamic behavior of networks of interacting elements can in principle be modeled by sets of differential equations which solves equilibrium states and dynamic responses of the system to perturbations. For example, the behavior of chemical mixtures can be solved in terms of concentrations and chemical reaction constants (presenting the interactions). The behavior of interlinked biological pathways were described in relation to metabolic cycles and their control [Chock and Stadtman, 1977]. Features like amplification and non-linear response, feedback and temporal integration all emerge from the interlinking [Hjelmfelt et al. 1993]. However, it is rarely the case that sufficient information exist to discribe complex biological mechanisms in the level of details required for such dynamic modeling. A number of recent works have applied neural networks to model biological pathways like receptor mediated signaling of bacterial chemotaxis [Bray et al. 1993], and segmentation in the embryonic development of Drosophila, [Burstein, 1995]. These works used the known hierarchical structure of the molecular mechanisms to build neural networks that model the behavior of the studied biological systems. One purpose of the present invention is to do the inverse of common neural network analyses, namely to deduce about the hierarchical network structure of the studied biological mechanism from the analysis of the raw experimental measurements.

SUMMARY OF THE INVENTION

An object of the invention is to characterize a complex system by analyzing multivariable measurements under controlled set of conditions and estimating weight parameters indicative of relations between these variables characterizing components of the studied system.

Another object of the invention is to sort sets (vectors) of simultaneous measurements of many variables based on the linked behavior of components, thus forming fingerprints of complex states of the system.

Another object of the invention is to extract the hierarchy of inducing and inhibiting interactions between components, based on time dependent or dose dependent changes of variables in response to perturbation or stimulation. It is the linked responses of cellular components and their temporal order that discloses the information about the network of relationships reflecting functional interactions between these components and their hierarchy.

These and other objects and advantages are achieved by the method and apparatus according to the invention, in which a simple (single-layer) neural network is applied to analyze measurements of variables characterizing components of a complex system. The neural network is trained by the measured data and gives a matrix of weight parameters that quantifies relations between variables, points on those most relevant to the studied process, and proposes hierarchical skeleton structures of network of interactions between these components that underlie the behavior of this system.

According to the invention a computerized platform is used to analyze the dependencies of measured variables on induced perturbation or stimulation or on controlled conditions. The analysis applied to steady state conditions creates a mechanism to fingerprint data sets, recognize and sort complex patterns of measurements and highlight key components which are most important for sorting the various states. When applied to time dependent experiments the dynamic analysis can further outline a hierarchy of relations between the components, construct a skeleton network of interactions that governs the logical structure of the studied process and quantify their strength. The results are given numerically, quantifying relations between variables, and by color-coded presentations in which dominating positive and negative weight parameters are easily identified, and by hierarchical skeleton graph of the interaction network.

What is special about this invention which was never explored in the art of neural networks will now be explained. Let us consider a simplified case of measured concentrations of three molecules in control cells and in cells incubated with a drug. The first two concentrations did not change, the third one doubled. The action of the drug on the cells can be presented by the linear operation of a weight matrix, $W$, multiplying a cell state vector, $C$, composing of the three concentrations, $C'=WC$. Obvious solution for $W$ is:

$(c1)$ $(1\ 0\ 0)(c1)$ $(c2)=(0\ 1\ 0)(c2)$ $(2*c3)$ $(0\ 0\ 2)(c3)$

However, given the above data there are many other solutions for the matrix $W$ that will act on $C$ to yield $C'$. For example for all $x$ and $y$, as large as we wish, that supply the relation $x*c1-y*c2=0$ we shall also have:

$(c1)$ $(1\ 0\ 0)(c1)$ $(c2)=(0\ 1\ 0)(c2)$ $(2*c3)$ $(x\ y\ 2)(c3)$

While the rigorous answer spans infinite number of possible solutions, and a neural network learning process may converge to any of them, it is possible to define a single solution characterized by minimal variance of the parameters. A numerical method to obtain this generalized matrix inversion solution for the linear case uses singular value decomposition, or SVD [e.g. Press et al. Numerical Recipes]. It is one purpose of this invention to generalize such approach to non-linear relations between measured variables. This solution may present the maximum information available from a given set of measurements, since it explores the space of possible solutions and zeroes variables that are free to fluctuate up and down, but coherently accumulates variables that are truly constrained by the data. In the above example, the data point to the fact that $c1$ and $c2$ present the concentrations of molecules that do not respond to the action of the drug. This can clearly be seen from $W$ only in the "minimal variance" solution, while solutions reached by any of the training epochs common in the art of neural network may include large elements such as $x$ and $y$ above. While this example is trivial, it outlines the problem in the general case, where clear separation of "relevant" and "irrelevant" measurements cannot be extracted directly by looking at the data, due to noise and to inter-related behavior resulting from the biology. The invention describes a method that computes weights scoring the "relevance" of each measured variable.

Cellular behavior depends not only on concentrations of the molecules involved, but also on subcellular localization, modification of the molecules, concentrations of cofactors etc. Many of these properties are either unknown or cannot be quantitatively characterized for use in mathematically rigorous modeling. Moreover, it is often the case that some of the molecules involved in a biological mechanism are not known at all or are not accessible to measurements. Therefore, biological measurements (even those oriented towards context-wide multiparameter characterization such as DNA chips) almost always constitute an under-defined problem, and therefore a unique solution can only be defined if additional constraints are imposed. Here the biologically logical constraint excluding wildly fluctuating values allows to define a method to reach a unique solution for the weights even in under-defined cases.

The invention employs single-layer neural network learning algorithms to explore the space of possible weight matrices for the non-linear case, and from this define the solution for the weights. Neural network algorithms teach methods to iteratively converge to weight matrices relating input and output data sets ("training epochs"). However, in the art of neural network applications all weight matrices that act on input sets to yield the same outputs serve equally well. Therefore there is no concern that the weights to which a training process converge will depend on the initial guess for a solution. The present invention describes how to construct a weight matrix that not only relates measured inputs to outputs, but present usable estimates for the relations (or generalized interactions) between input and output variables, from which one can read the measured variables most relevant to a process and draw pathways describing the mechanism explored by these measurements.

There are two embodiments for the usage of the method:

In the first embodiment cellular "states" are characterized by measurements of many cellular changes induced when cells are stimulated to proliferate or to differentiate. The invention is used to obtain a weight matrix that emphasizes changes relevant for proliferating cells as opposed to differentiating cells, so that unknown cells could be sorted according to the operation of this weight matrix on its measured cellular changes. Again as a trivial example, if proliferating cells show increase in variable A, and differentiating cells increase in variable B, the weight matrix should include non-zero weights of opposite signs for these variables only. Since the pattern of changes in proliferating and differentiating cells is complex, with many overlapping components, the invention describes a method to fingerprint such multivariable patterns sorting them into one of a list of cellular states.

In the second embodiment the measurements follow dynamically cellular changes (here in phosphorylation levels) in response to a stimulus. The invention is used to obtain a weight matrix that describes the interactions between the measured components giving rise to the dynamic behavior. The weight matrix is used to "reverse engineer" the pathway from the measurements and present it graphically by lines corresponding to positive (inducing) and negative (inhibiting) weights (interaction strength) connecting the molecules for which changes was measured. The invention is suited in biology to study the effects of stimuli such as drugs, mutations, growth factors or hormones, forced expression of proteins and the time dependence of these effects, and characterize cellular states in controlled conditions such as cell starvation, proliferation, differentiation, transformation and appoptosis. It is therefore applicable to basic biological research (in fields such as cell cycle, signaling pathways, development and cell fate determination), to biomedical areas (screening of drugs, optimization of cocktails for chemotherapy, typing of tissues and cancers, etc.) as well as to analyses of complex ecological and financial systems.

The method and apparatus are briefly presented, illustrated by examples, and applied for two characteristic biological problems using available data, one for identifying steady state fingerprints correlated with proliferation due to mitogenic induction, and the second using dynamic data for drawing the hierarchy of interactions in the signal transduction pathway of insulin.

The invention comprises apparatus for analyzing multivariable data sets including a plurality of measured variables, said apparatus comprising:

a neural network capable of receiving signals contained in said data sets and processing said signals according to an artificial intelligence program; and means for obtaining a matrix of weight parameters for said neural network and said data sets through a sequence of iterations, starting at random guess, and repeatedly averaging for many initial guesses until said matrix of weight parameters converge; and means of evaluation of the relationship between said variables from said weight parameters.

The invention further comprises apparatus as above wherein said data sets comprise experimentally determined data which characterize variations in measurable components of a biological process. The invention can be used for fingerprinting complex cellular states by analysis of cell responses to external stimuli, with the apparatus comprising:

means for collecting data sets which includes a plurality of induced and measured variables which characterize stimuli applied to cells and responses of said cells to said stimuli;

a neural network capable of receiving signals contained in said data sets and to process said signals according to an artificial intelligence program; and means for obtaining a matrix of weight parameters from said neural network, said weight parameters allowing identification of fingerprints of complex cellular states.

The invention can comprise apparatus according to the above wherein said external stimulus may be for example a drug, growth factor, hormone, a mutated proteins or forced expression of cellular component, and said complex cellular state is starvation, appoptosis, cell differentiation, mitogenicity of proliferating cells or cell cycle arrest.

The invention can comprise apparatus according to the above for construction of hierarchical architecture of interaction network between said components of said biological process by analysis of cell responses to external stimuli, comprising:

means for collecting time dependent data sets which includes a plurality of changing variables which characterize responses of said cells to said stimuli;

a neural network capable of receiving signals contained in said data sets and to process said signals according to an artificial intelligence program; and means for obtaining a matrix of weight parameters from said neural network, said weight parameters allowing the construction of hierarchical architecture of said interaction network. The network can be a signaling pathway in cells.

The neural network matrix of weight parameters can be represented by a color coded image, in which dominating positive and negative weight parameters are easily identified.

The neural network can be comprised of a matrix of weight parameters $W_{ji}$ which operate on input variables $I(k)_j$, through a monotonic transfer function to generate output variables $O(k)_i$, according to:

$$O(k)_j = f\left\{\sum_{i=1,N} W_{ji} * I(k)_i + B_j\right\} (k = 1, L; j = 1, M) \quad \text{(Eq. 1)}$$

The method or process of the invention for analyzing multivariable data sets including a plurality of measured variables, said process can comprise:

providing a neural network;

applying signals representative of variables contained in said data sets to said neural network and processing said data in a sequence of iterations, starting at random guess for said neural network matrix of weight parameters, and repeatedly averaging until said matrix of weight parameters converge; and generating from said matrix of weight parameters an evaluation, indicating relationship between said variables.

In the process according to said the above, the neural network can be comprised of a matrix of weight parameters $W_{ji}$ which operate on input variables $I(k)_j$, through a monotonic transfer function to generate output variables $O(k)_i$, according to:

$$O(k)_j = f\left\{\sum_{i=1,N} W_{ji} * I(k)_i + B_j\right\} (k = 1, L; j = 1, M) \quad \text{(Eq. 1)}$$

Further the inventive method can be comprised of the steps of obtaining a data set comprising a plurality of input/output multivariable vectors representative of a biological process involving many interacting multifunctional components in at least one pathway, establishing a neural network comprised of single layer network operators, applying the data set to the neural network, training the neural network by a training algorithm to implement a transformation by a matrix of weights starting with a first random guess and iteratively modifying according to a learning rule until the weight matrix comes to convergence and produces a solution, then, using successive random guesses, repeating the training for each random guess until the weight matrix comes to a convergence solution for each random guess whereby a plurality of weight matrix solutions are obtained, averaging the weight matrix solutions to obtain an averaged weight matrix, determining from said matrix of weights the hierarchical structure between said components.

In the inventive method the hierarchical structure is portrayed by drawing the vectors between the variables as determined by the magnitude of the matrix of weights. Also, weights smaller than a preselected threshold can be ignored in the portrayal. Still further, the data set of input/output multivariable vectors constitutes time dependent data. The data set can include an input set including a measured set of variables at consecutive times, and an output set comprised of the same data as the input set, but shifted forward in time to a later time, so that the neural network learns to take in data at one time and give out data at the later time.

The inventive method can comprise the steps of obtaining a data set comprising a plurality of input multivariable vectors representative of a biological system involving many interacting multifunctional components in at least one pathway, that define a complex biological state (or condition), determining a corresponding output vector for each input vector that defines classes for the input vectors, establishing a neural network comprised of single layer network operators, applying the data set to the neural network, training the neural network by a training algorithm to implement a transformation by a matrix of weights starting with a first random guess and iteratively modifying according to a learning rule until the weight matrix comes to convergence and produces a solution, then, using successive random guesses, repeating the training for each random guess until the weight matrix comes to a convergence solution for each random guess whereby a plurality of weight matrix solutions are obtained, averaging the weight matrix solutions to obtain an averaged weight matrix, modifying the neural network to set its transformation of a matrix of weights to the averaged weight matrix, whereby the modified neural network can sort newly presented input vectors into the classes that were defined by the output set of vectors in the training.

In the method above a multitude of random guesses are used and a multitude of weight matrix solutions are obtained which are averaged to obtain the averaged weight matrix.

Further the invention comprises apparatus for processing input vectors representative of a biological process involving many interacting multifunctional components in at least one pathway comprising, a neural network composed of single layer network operators trained by a training algorithm to implement a transformation by a matrix of weights, the training including starting with a first random guess and iteratively modifying according to a learning rule until the weight matrix comes to convergence and produces a solution, then, using successive random guesses, repeating the training for each random guess until the weight matrix comes to a convergence solution for each random guess whereby a plurality of weight matrix solutions are obtained, and then averaging the weight matrix solutions to obtain an averaged weight matrix, said neural network having been modified so that the neural network is set to its transformation of a matrix of weights to perform its function based on the averaged weight matrix, so that the modified neural network will give a predetermined output vector for a predetermined input vector that presents a prescribed pattern of values, and a mechanism for inputting vectors into the modified neural network, and to receive output vectors from the modified neural network.

The inventive apparatus above can include a device for recognizing a predetermined input vector based on the output vectors received by the mechanism. Also, the input vectors can be sorted according to predetermined criteria for the output vectors.

The invention relates to a method and apparatus for analyzing multivariable data sets in which, a general computerized platform is provided for evaluating the relationship between large number of measurements of sets of variables characterizing components of complex states of a system under induced stimulation or controlled conditions. The linked responses of variables and their temporal relations tell about the network of interactions and their hierarchy. Processing of data sets by a simple neural network gives a matrix of weight parameters, that allow to identify fingerprints of complex states characterized by patterns of measured variable and estimate the interactions between the components characterized by the measured variables. The results are provided numerically and by color-coded presentation indicating dominating relations between variables and strongly responding variables. When applied to dynamic responses of a system, the analysis can construct a schematic hierarchical architecture of the network of interaction between the components of the studied system. Applications in biology include analysis of measurements characterizing responses of molecular components in cells under changes induced by stimuli (e.g. drugs, growth factors, hormones, mutations or forced expression of a proteins), and identification of complex cellular states (e.g. proliferation, differentiation, transformation, starvation, necrosis, apoptosis, and the time dependencies of the above effects).

Other objects, advantages and novel features of the present invention will become apparent from the following detailed description of the invention when considered in conjunction with the accompanying drawings.

BRIEF DESCRIPTION OF THE DRAWINGS

FIGS. 2(A)–2(G) are graphic depictions corresponding to FIG. 1, which show examples of input and output data sets for various network architectures and the corresponding matrices of neural network weight parameters. These basic structures form the basis for drawing graphically a complex network structure from the weight matrix;

FIG. 3 is a schematic block diagram of apparatus for analysis of multivariable data sets according to the invention, see also the flow chart;

FIG. 7(B) is a schematic depiction of the hierarchical skeleton structure graphically presenting the network of interactions in the insulin signaling pathway deduced from the weight parameters corresponding to FIG. 7(A) as listed in Table 3.

DETAILED DESCRIPTION OF THE PREFERRED EMBODIMENTS

Each layer of a neural network is composed of a matrix of weight parameters, $W_{ji}$, operating on sets of input variables, $I(k)_i$, and computes sets of output variables, $O(k)_j$, [Beale and Jackson, 1990]:

$$O(k)_j = f\left\{\sum_{i=1,N} W_{ji} * I(k)_i + B_j\right\}(k = 1, L; j = 1, M) \quad \text{(Eq. 1)}$$

Figure 1:
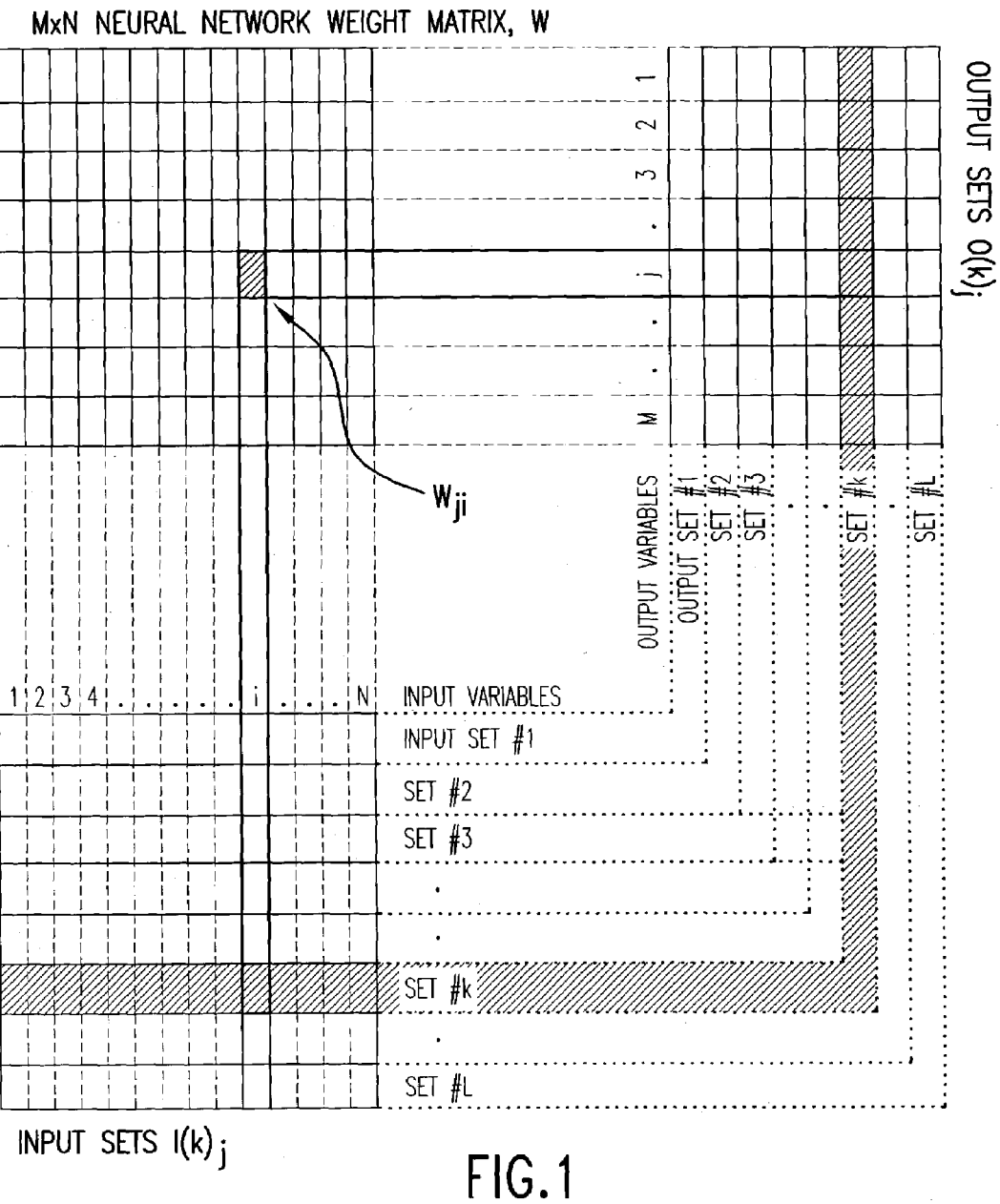
FIG. 1 illustrates schematically the arrangement in all following figures of the input and output multivariable data sets and of the matrix of neural network weight parameters.

A neural network implements a matrix transformation. As illustrated in FIG. 1, the number of variables in the input sets, N, the number of variables in the output sets, M, and the number of such sets, L, may be arbitrary, depending on the problem. f is a monotonic function (the transfer function), and $B_j$ are the bias parameters. The transfer function extends the capability of neural network algorithms beyond simple linear algebra.

FIG. 1 relates the input and output variables to the weight parameters in the corresponding column and row of the matrix W. In conventional matrix algebra notation, a matrix of dimensions M×N multiplies an input column vector of dimension N to yield an output column vector of dimension M. In order to visually relate the weight parameters to the input and output variables, the input vector sets in FIG. 1 are rotated and presented below the matrix W such that every matrix element $W_{ji}$ (shown dark) presents the weight parameter relating an input variable i in the corresponding vertical column with an output variable j in the horizontal row. Corresponding input and output data sets are connected by dotted lines in FIG. 1. For example, when the neural network is presented with input set k, it computes output set k, both of which are shown shaded.

Neural networks can be trained (learning phase) to produce prescribed outputs (or Targets) when presented with given inputs. In this training process, the weight parameters and the biases are the fitted parameters, iteratively modified by a corrective formula (learning rule) starting from an initial guess. If they reach to obey the above equation exactly for L sets of input and target values, the network is said to be trained. Examples for training algorithms are Perceptrons for a theta (step) transfer function, ADALINE for a linear transfer function and backpropagation for non-linear transfer function [Demuth and Beale, 1993].

For a linear transfer function, the matrix of weight parameters converged following iterative training can be also computed by generalized matrix inversion (for example using singular value decomposition, SVD) or least square best fit for L larger than N and M. For small L there is no unique solution though, and the trained network parameters depend on the initial guess. Yet, by averaging on many random initial guesses, irrelevant variables are averaged to zero, and a unique solution is approached. The lows of averaging random numbers make it possible to assign error bars to the results, and thus ascertain that the only source of errors is experimental, and can be estimated from repeated measurements.

Explaining in greater detail, the single layer Neural Network (NN) implements a transformation operating on a set of L input vectors, I, [I are N-dimensional vectors, I=$I(k)_i$ is the i-th component of the k-th input vector] and computes a set of L output vectors O [O are M-dimensional vectors, O=$O(k)_j$ is the j-th component of the k-th output vector].

A single layer NN transformation can be written as:

$$O(k)_j = f\left\{\sum_{i=1,N} W_{ji} I(k)_i + B_j\right\} (k=1, L; j=1, M) \quad \text{[Eq. 1]}$$

$W_{ji}$ is the weight matrix, $B_j$ are bias parameters and f is a monotoneously increasing function (Beale and Jackson, 1990; Demuth and Beale, 1993).

Given a set of input vectors, I, and a corresponding set of target vectors, T, to which the output vectors should match, [T are M-dimensional vectors, $T=T(k)_j$ is the j-th component of the k-th target vector], NN training is based on iterative process that progressively corrects the weights and biases so that each iteration reduces the difference between target sets T, and the output sets O obtained from the NN transformation on the given input vectors sets I. For example, the corrections for the weights and biases according to Widrow-Hoff adaptive linear network (ADALINE) training rule (Widrow and Stern, 1985) are:

$$W_{ji} = \left[\sum_{k=1,L} T(k)_j - O(k)_j\right] I(k)_i \quad \text{[Eq. 2]}$$

$$B_j = \left[\sum_{k=1,L} T(k)_j - O(k)_j\right] \quad \text{[Eq. 3]}$$

is a small number, so that the small steps that modify the weights and biases follow the local gradient that minimizes the difference between T and O progressively. NN training starts at any randomly chosen initial guess, and ends at the closest minimum. As is well known for multiparameter functions, their values form a complex landscape with many local minima which trap the minimization process yielding different solutions for different initial guesses. Moreover, when the problem is ill-posed, [e.g. for the case that f is a linear function, either since N>k (more unknowns than equations) or the equations are linearly dependent] the iterations will reach arbitrarily one of an infinite number of solutions.

This fact did not pose a problem for conventional NN practice. The reason is that all solutions minimize equally well the difference between T and O, [the weights are hidden in a black box trained to transform input vectors to output targets]. The application of the present invention asks to open the black box and search for the "important" weights. This requires defining a unique solution between all possible ones for the weights. This novel feature of the invention is achieved by imposing a constraint on the solution which emerges from the biology. Each weight models a "connectivity" or generalized interaction between an input and an output variable. Although generally connectivity of every input to every output variable is possible, according to the invention the biologically plausible solutions are those with only few connectivities to each variable, and out of all different solutions, the biologically relevant one should minimize the variance for the weights. This precludes the mathematically legal solutions with two large weights that act on input vectors to mutually cancel each other. According to the invention, this constraint implies that largest weights present the most important "interactions" between input and output variables.

The method according to the invention, as used here to reach such minimal variance solution, is to repeatedly average many NN solutions that were obtained by the usual NN training methods, but each initialized at randomly chosen values for the weights, thus sampling the space of all possible solutions. Weights that are free to vary since they compensate each other's effects will be averaged to zero, while weights that stay consistently large, (positive or negative) are coherently averaged to a value that reflects their "importance" in this transformation, and connects input and output variables most relevant to the process through which these variables were measured.

Typically, NN training starts at an initial guess and requires 100 iterations to converge to a solution. According to the inventive method, the averaging repeats the NN training process many times, each training process is initiated at a random guess for the weights, and reaches a solution. The solutions of the multiplicity of training processes are usually different. The Average of all these solutions reduces the values of weights that are free to vary. Practice of the inventive method showed that an Average based on 100 randomly initiated guesses reduces such weights to 10% of their variance [or 1000 trainings averaged reduces to 3% based on the variance of random numbers]. Since in the examples that follow the largest weights were selected by ignoring weights smaller than 1/10 of the largest one, 1000 weight solutions were averaged and used.

Once trained, the neural network can be presented with yet uncharacterized input sets (recognition phase) to give new output sets that identify and sort input data patterns. This application of neural networks enables to define multivariable fingerprints of complex data patterns corresponding to cellular states. Most powerful applications of this kind split the task of interpretation and sorting of input data into several layers of consecutive operation of Eq. 1 (above). Yet, the present invention extracts useful information also from the matrix of weight parameters, rather than only applying the previously trained neural network as a black box mathematical sorting operator. For this purpose, the use of neural networks here is based on the simplest single layer network operators. At least at the first stage, modeling by multilayer networks is avoided since this imposes a priori architecture that should reflect known decision making flowcharts and pathway schemes. Rather, it is preferable to deduce the network architecture from the neural network matrix of weight parameters.

The basis for such deduction from a single layer neural network can be illustrated by the simplified examples shown in FIGS. 2(A)–2(G), in which a set of measurements of five variables a, b, c, d and e quantify the state of activation of events A, B, C, D and E respectively. The input and output data sets are both composed of these same five variables. If a set of input values $(a_1,b_1,c_1,d_1,e_1)$ is presented to the neural network, the output set with values $(a_2,b_2,c_2,d_2,e_2)$ denotes the measurements following activation of ABCD and E according to the values in the input set.

The panels in FIG. 2 show neural network weight parameter matrices that correspond to various logical structures of response. For simplicity, the variables are normalized between 0 and 1, and the transfer function is a step function: $f(x<1)=0; f(x>1)=1$ (Perceptrons). Only non-zero elements are marked.

Figure 2A:
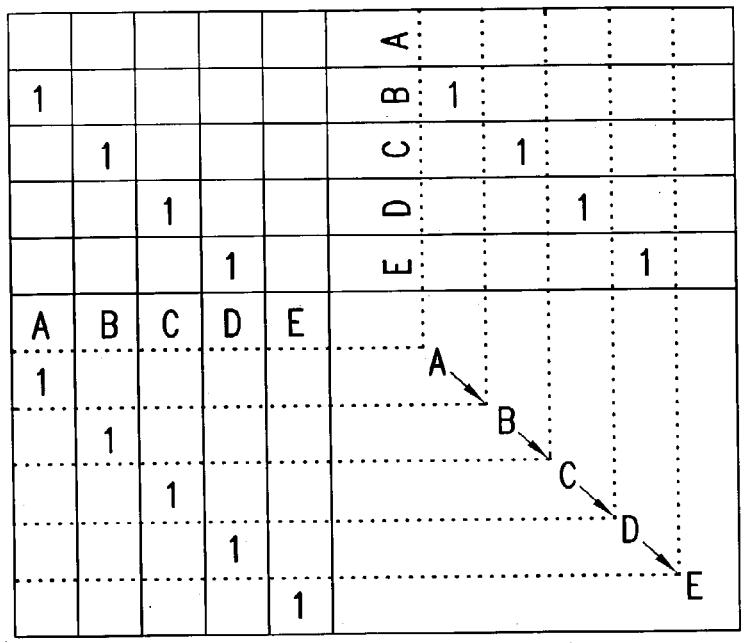

FIG. 2(A) shows a cascade: A induces B, B induces C, etc. The neural network matrix of weight parameters displays an off-diagonal arrangement of large weight parameters, cross-linking the activation of one event to the induction of the next one downstream.

Figure 2B:
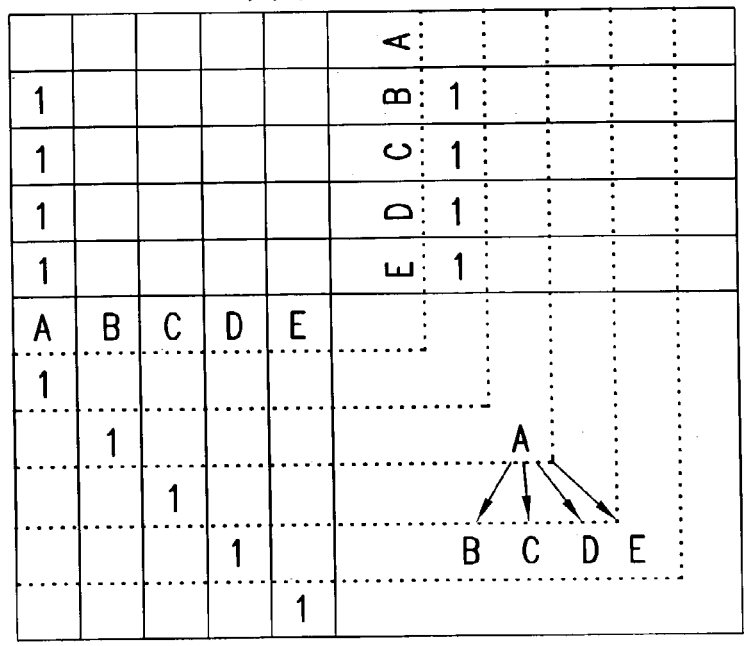

FIG. 2(B) shows a diverging network structure. In this case, the activation of A induces all the events B, C, D, and E. The corresponding matrix displays large weight parameters at its first column corresponding to the input variable A.

Figure 2C:
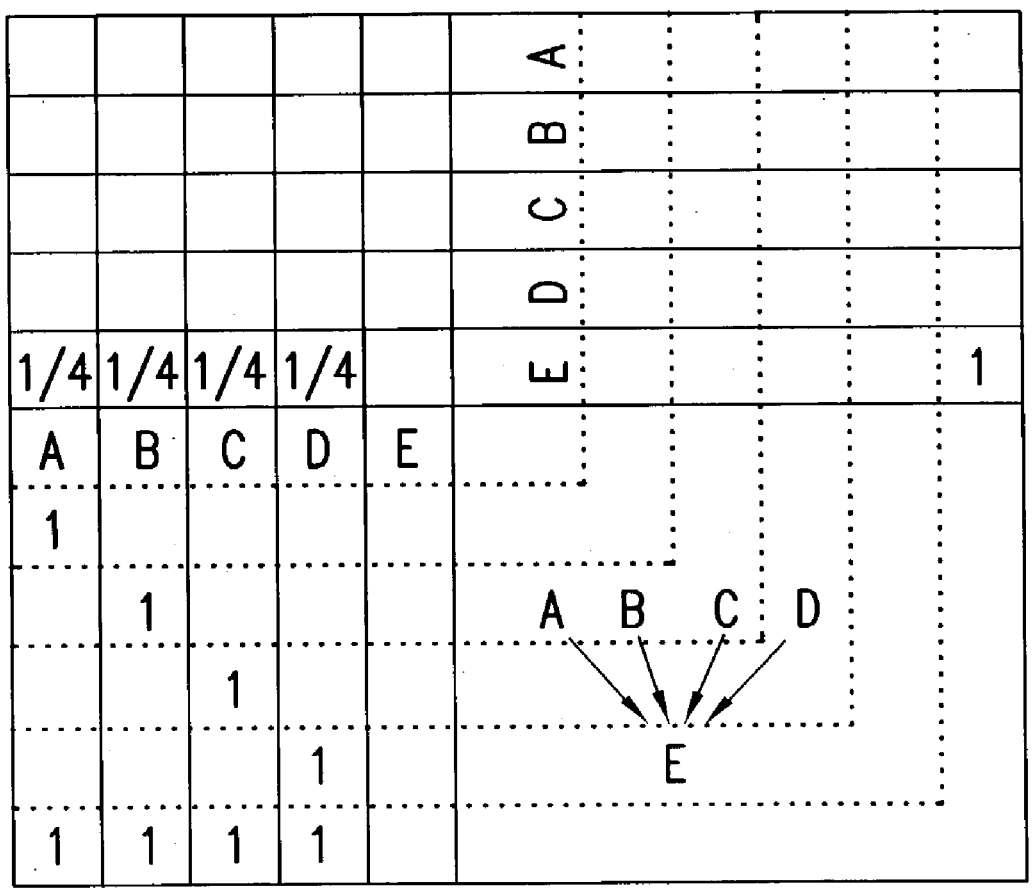
Figure 2D:
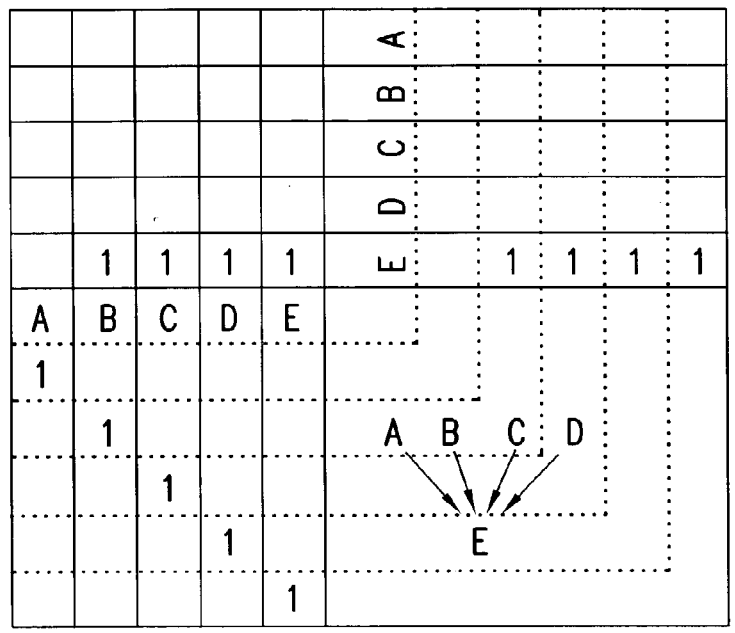

FIGS. 2(C) and 2(D) show converging network structure in which A,B,C, and D induce E. There are two extreme kinds of such structure, and for both the neural network matrix displays large weight parameters in the row corresponding to the output variable E. FIG. 2(C) shows an integrative pathway, in which more of A can compensate for less of B, but several are still required simultaneously, since saturated levels of A,B,C or D cannot alone activate E. FIG. 2(D), on the other hand, illustrates an alternative converging pathway, meaning that activation of one of the events A,B,C, or D can by itself induce E.

Figure 2E:
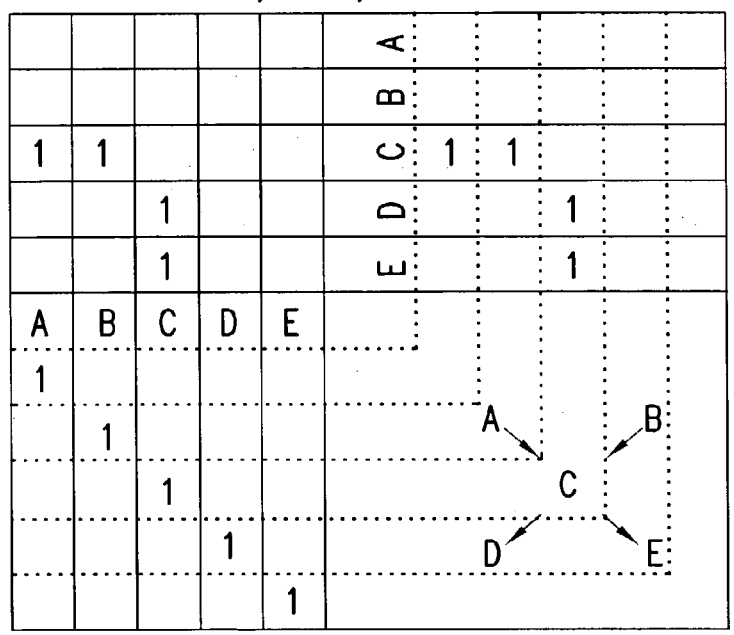

FIG. 2(E) shows a nodal point (or a checkpoint) in event C. A node is the meeting between converging and diverging network structures; thus it is clearly displayed in the neural network matrix as a cross between a row and a column of large weight parameters.

The above examples are the kind of analysis that applies to the steady states of activated components before and after a stimulation or induction of a change. FIGS. 2(F) and 2(G) are examples of time dependent data, where each output set serves as the next time input data set. Logarithmic time data sampling is appropriate for exponential time dependencies, and can cover seconds to days of cell response dynamics in a small number of sets. FIG. 2F) is an example of a transient, induced through a cascade of events A,B,C,D & E. The off-diagonal parameter controls the dynamics (being the fractional change in consecutive time measurements). FIG. 2(G) is the neural network weight parameter matrix that presents a sustained activation of the above cascade of events. The neural network matrix becomes triangular. Clearly one expects intermediates between FIG. 2(f) and FIG. 2(g), with triangular weight parameters decaying farther away from the diagonal, depending on the ratio between the rate of changes and the measurement sampling times.

These examples indicate that the dominating weight parameters in a trained neural network matrix can be directly related to the hierarchical skeleton of the network of interactions responsible for the activated events in a responding system. In reality, when applied to cellular responses, stronger skeletal structures will be connected with less strong interactions to other components of the input and output sets. The weaker such interactions are, the more precise data is needed to extract them reliably. The color coded display of the weight parameters such as in FIGS. 4 and 6 helps identify visually the largest positive (red) and negative (blue) elements. From a hierarchical listing of the magnitude of these interaction parameters it is possible to estimate the inducing and inhibiting interactions between components and reconstruct in terms of these components the logical structure of the mechanism corresponding to the network (see example 2 and FIG. 7(B)).

FIG. 3 is a schematic block diagram of the system for analysis of multivariable data according to the invention. The flow chart below details the possible steps for each block.

Flow Chart Summarizing the Steps in the Analysis of Data.

Data can be analyzed using commercially available software such as MATLAB® Neural Network Toolbox [The MathWorks, Inc. Natick, Mass. 1993], but here specially written software was used.

1. Measurements→Experimental Data.
2. Neural Network Interface:
    Raw Data→Input/Output Sets.
    I. Arrange corresponding input and output sets.
        e.g.: Input: sets of measurements.
            Output: grades for resulted states of the system.
        Or: concentrations of drugs.
            e.g.: Input: sets of measurements.
                Output: measurements in consecutive times.
    II. Align same variable in all data sets (see FIG. 1.)
    III. Scale, average, normalize or take differences of variables
    IV. Add identifying labels to variables
3. Neural Network Training:
    Input/Output Sets→Weight Parameters.
    Select training algorithm (Perceptron, ADALINE, Backpropagation)
    Averaging results initiated at random weight parameters and biases
    Initialize W and B
    Apply training Rule and iterate until W and B converge
    Repeat averaging till fluctuations fall below a required value
4. Analysis:
    I. Color-coded display neural network weight parameters matrix
        →visualization of most relevant variables
        →permutation of variables in hierarchical order
    II. List of the weight parameters ordered by magnitude
        →evaluate strength of inducing/inhibiting interaction
        →identify key parameters for a skeletal structure
        →construct hierarchical architecture of network skeleton
    II. Presentation of new input sets
        →fingerprinting and sorting.

As shown in FIG. 3 and in the flowchart, the experimental data M consist of a large number of measurements. The data are entered into the neural network through an interface I. They are organized and aligned in input and target (output) data sets, variables are labeled, averaged, scaled, normalized or differences taken. The neural network N may be implemented in the form of a general computer platform trained in a manner known to those skilled in the field of neural networks, using the input and target data sets and applying, for example, Perceptrons, ADALINE or Backpropagation learning rules. After repeated iteration and averaging on random initial weight parameters, this process converges to yield a matrix of weight parameters. The following analysis A employs these weight parameters for fingerprinting, operating on new input data sets and using the output to identify or sort patterns in input variables. The largest weight parameters point at the most relevant variables and their linked behavior, indicate interactions between the corresponding molecules, and propose an hierarchical architecture of interactions underlying the studied process.

As noted above, the molecular mechanism underlying cell signaling pathways is a biological problem that fits the scheme of well defined inputs that induce measurable output responses. Since many examples can be found in literature, two will serve here for the demonstration of the kind of analyses possible.

EXAMPLE 1

Analysis of Growth Hormone Data

In this example we show an application of neural networks to growth factor signaling demonstrating its use as a method for fingerprinting complex states, such as proliferating cells induced by mitogenic signals, sorting multivariable patterns of data sets into identifiable groups. We used published two dimensional gel maps of phosphorylation [Romano et al. 1994] shown here in FIG. 4(a). Romano et al. [1994] quantifies the phosphorylation of 60 proteins in two NIH3T3 cell constructs expressing epidermal growth factor (EGF) receptor in the first, and erbB-2 chimeras with extracellular EGF receptor fragment in the second. The intensities of the phosphorylated spots as a result of exposure to EGF, are given in Tables 1 and 2 of Romano et al. [1994], which are set forth as Tables 1 and 2 below. For each of the two constructs the phosphorylation levels were evaluated from both radioactive phosphate [$^{32}$-P] and from anti-phosphotyrosine antibody [p$^y$] blot, thus giving four input sets of data shown herein in FIG. 4(B). Each such set consists of 60 component variables, corresponding to the 60 identified spots in the two-dimensional gels shown in FIG. 4(A) and denoted as 1–32, A–Z. alpha and beta. As seen in Tables 1 and 2, one of five possible levels of phosphorylation were assigned to variables (+++, ++, +, ± and −) and used as input data sets encoded by red, orange, yellow, light green and green, respectively, in FIG. 4(B). The single output variable denotes mitogenic induction evaluated by cell proliferation. It is 100 times larger for the erbB-2 constructs (output data sets not shown).

An ADALINE neural network [Demuth and Beale, 1993] was used. The neural network matrix of weight parameters has dimensions 1×60. FIG. 4(C) shows the average of 200 solutions of weight matrices for neural network trained by the input and output data sets in FIG. 4(b), each converged following about 100 iterations starting from a random matrix. The total processing time on Silicon Graphics workstation is several seconds.

Figure 4A:
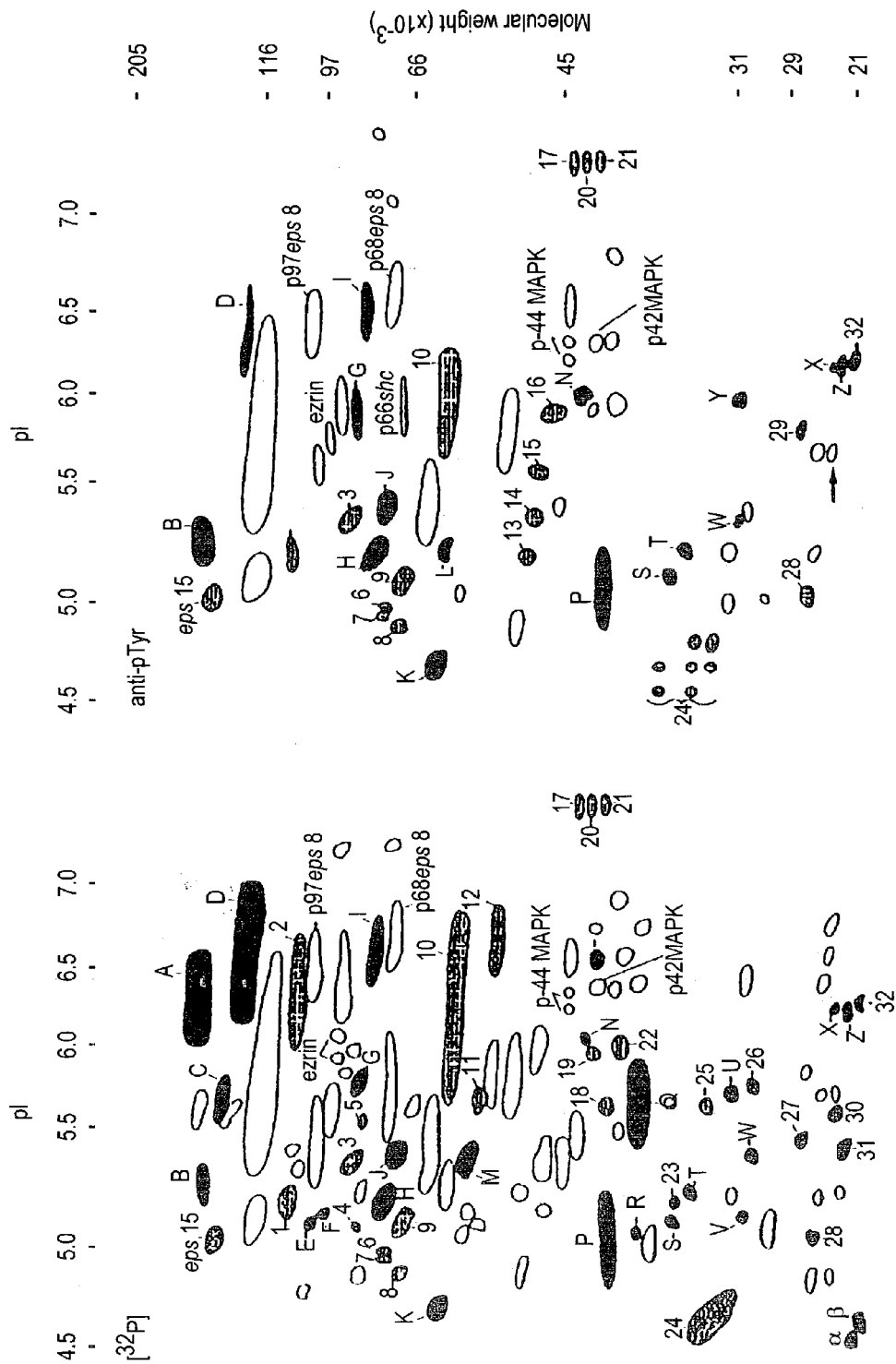
FIG. 4(A) is a graphic depiction of two dimensional gel maps for representative experiments from published literature [Romano et al. 1994] used for evaluation purposes.
Figure 4B:
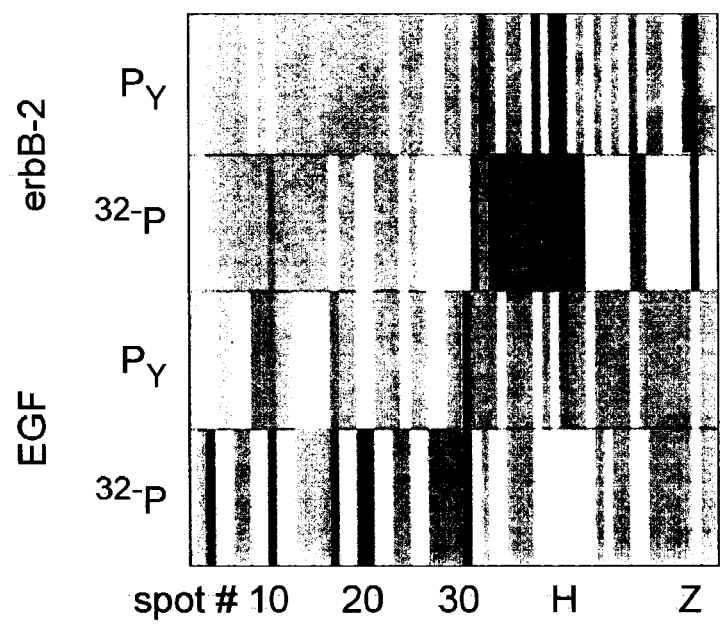
FIG. 4(B) is a graphic presentation of four input sets each having 60 components corresponding to the 60 gel spots quantified in gels as shown in FIG. 3A and given by the four columns of Tables 1 and 2. The purpose in this example is to use these vectors as fingerprints for sorting cellular states.
Figure 4C:
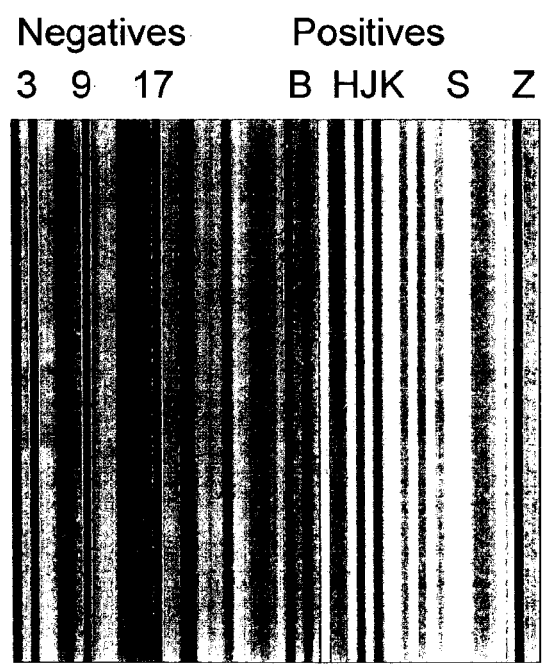
FIG. 4(C) is a color graphic depiction of the weights of the neural network trained by the input data sets in FIGS. 3(B) and output values of mitogenicity (or proliferateing index)

The analysis made by Romano et al concluded that the level of phosphorylation of two components, Paxillin (the spots designated H & J in FIG. 4(A)) and the yet unidentified protein Z, correlates with the erbB-2 phenotype of high mitogenic induction. The elements of the trained neural network (FIG. 4(C)) clearly learned this correlation, since the corresponding matrix weight parameters are indeed the largest (twice as large as the rest, indicated by black and red in FIG. 4(C)). Other spots found to correlate with mitogenic induction correspond to spots B, K and S in Tables 2. Interestingly, spots 3, 9 and 17 and other weaker spots in Table 1 strongly negatively-correlate with mitogenic induction (large and negative weight parameters indicated by dark blue in FIG. 4(C), comparable in their size to the positive parameters of spots H, J and Z, and not reported by Romano et al.), suggesting inhibiting molecular components in the growth induction signaling pathway, and raising the possibility that these components contain amino acid sequence motifs like Threonine, any two amino acids then Methionine [YXXM], that inhibit the induction of mitogenic signals via activation of the adaptor protein SHC [See Prigent and Gullick 1994].

This analysis creates a convenient fingerprint of mitogenic response of cell proliferation, integrates information collected in different measurements (two for this example, based on radioactive phosphate and phosphotyrosine antibodies), and identifies components which response is highly linked (positively- or negatively-correlated) with mitogenicity. Such data and analysis are unable though to specify whether these are primary events or secondary effects. What is missing for assigning hierarchies in the activation of molecular events is the time response.

Analysis of dependence on time makes it possible to obtain a network of inductive and inhibitive interaction parameters and assign hierarchy in the signaling pathway. This is demonstrated in the following example.

EXAMPLE 2

Analysis of Insulin Data

This example deals with time-dependent data measured at the Weizmann Institute [Biener et al. 1996]. The signaling pathway activated by insulin has been studied intensively. The events following insulin binding to its receptor (IR) include autophosphorylation, activating the kinase on its intracellular domain, with subsequent phosphorylation of insulin receptor substrates (IRS 1/2), proteins p60/62, src-homology-2-region containing proteins Shc46, Shc64 and Shc54, Annexin II, mitogene activating protein kinase (MAPK) and other unknown proteins. The insulin response of CHO cells transfected with the insulin receptor (about half a million per cell) was evaluated from phosphorylation levels using phosphotyrosine blots at various times following exposure to insulin [Biener et al. 1996].

Figure 5:
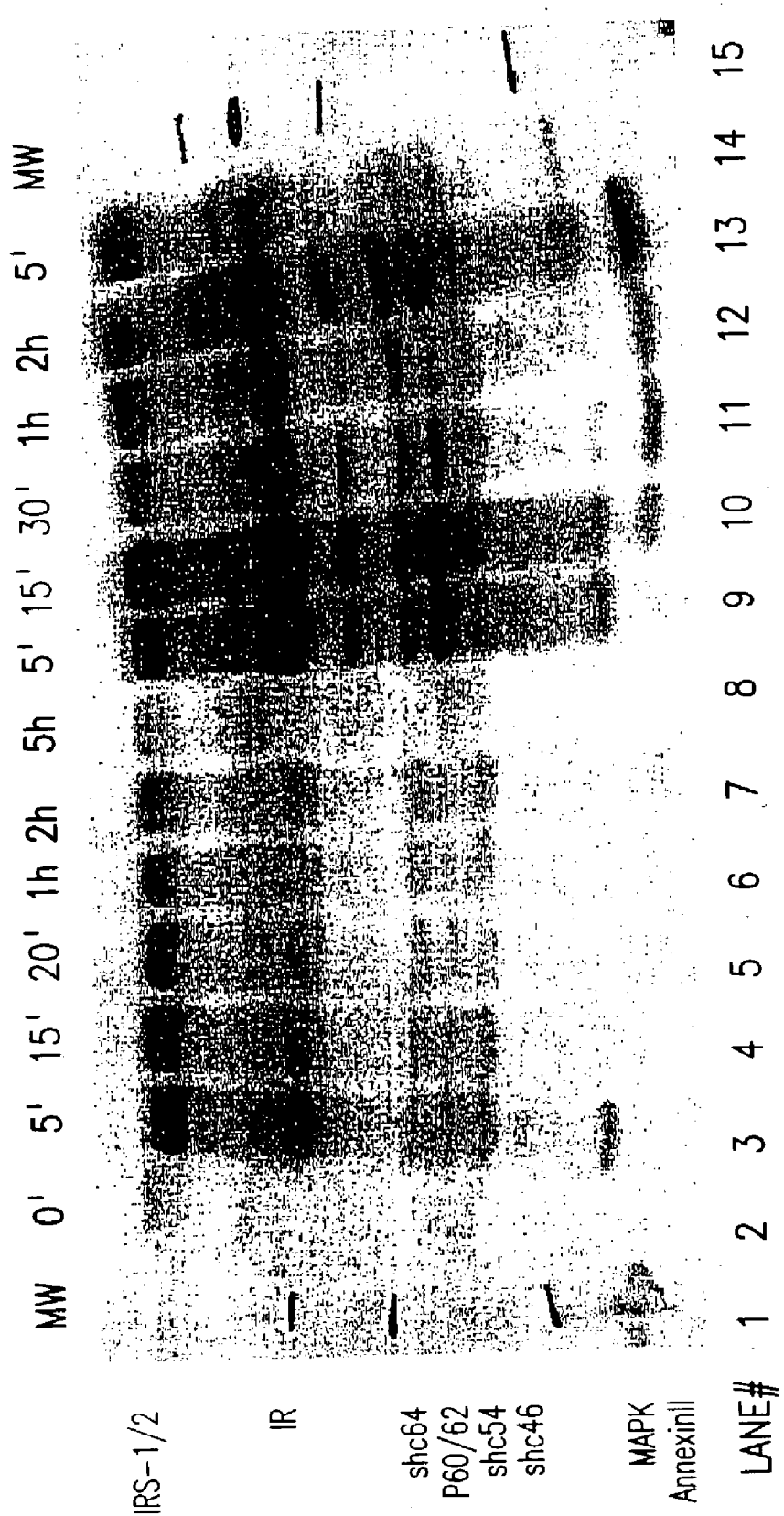
FIG. 5 depicts a time dependent phosphotyrosine gel blot of the response to insulin for Chinese hamster ovary cells (CHO) transfected with the insulin receptor from published literature [Biener et al. 1996]
Figure 6:
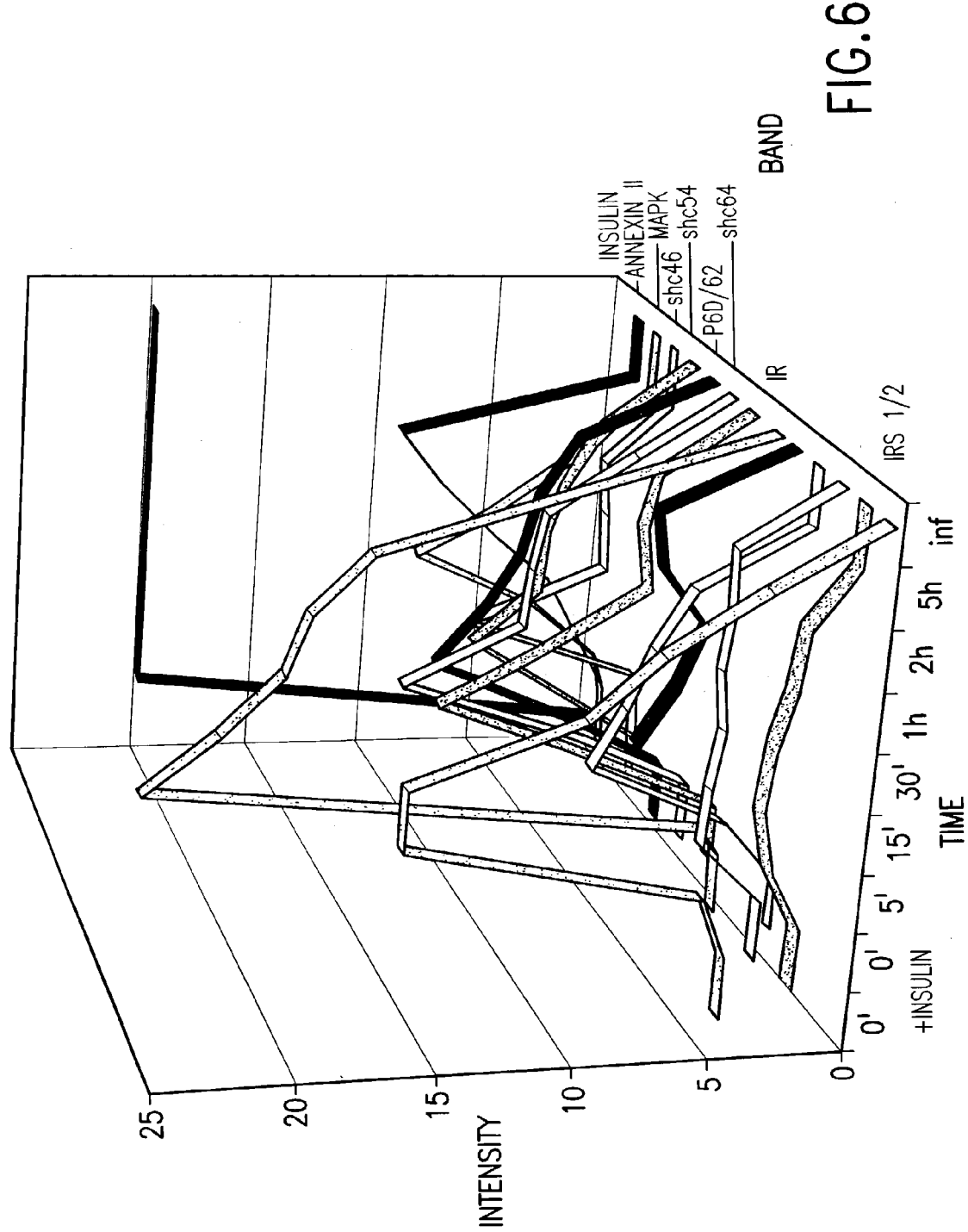
FIG. 6 is a graphic depiction of the time dependence of the phosphorylation levels of 13 resolved bands quantified and averaged in gels as in FIG. 4.

FIG. 5 shows a time dependent phosphotyrosine gel blot of the response to insulin. The gel blots reveal bands, some correspond to identified proteins and are marked, others are unidentified proteins. Lane 1 contains molecular weight markers. Lanes 2–8 correspond to 0, 5', 15', 20', 60', 2 h and 5 h incubation of the CHO cells with insulin followed by total cell extract gel loading and repeated at twice as high loading for lanes 9–13 at 5', 15', 30', 60' and 2 h and 5' again. Gel images were scanned and analyzed by the Quantity One software [PDI, Inc. Huntington Station, N.Y. 11746], to produce matched sets of 13 bands for all the lanes in the gel image. The phosphorylation levels display complex dynamics that are temporally lead by the insulin receptor phosphorylation and followed by slower processes with eventual down regulation of the insulin response. The time dependence of the insulin induced phosphorylation levels of the 13 bands is shown in FIG. 6.

Figure 7A:
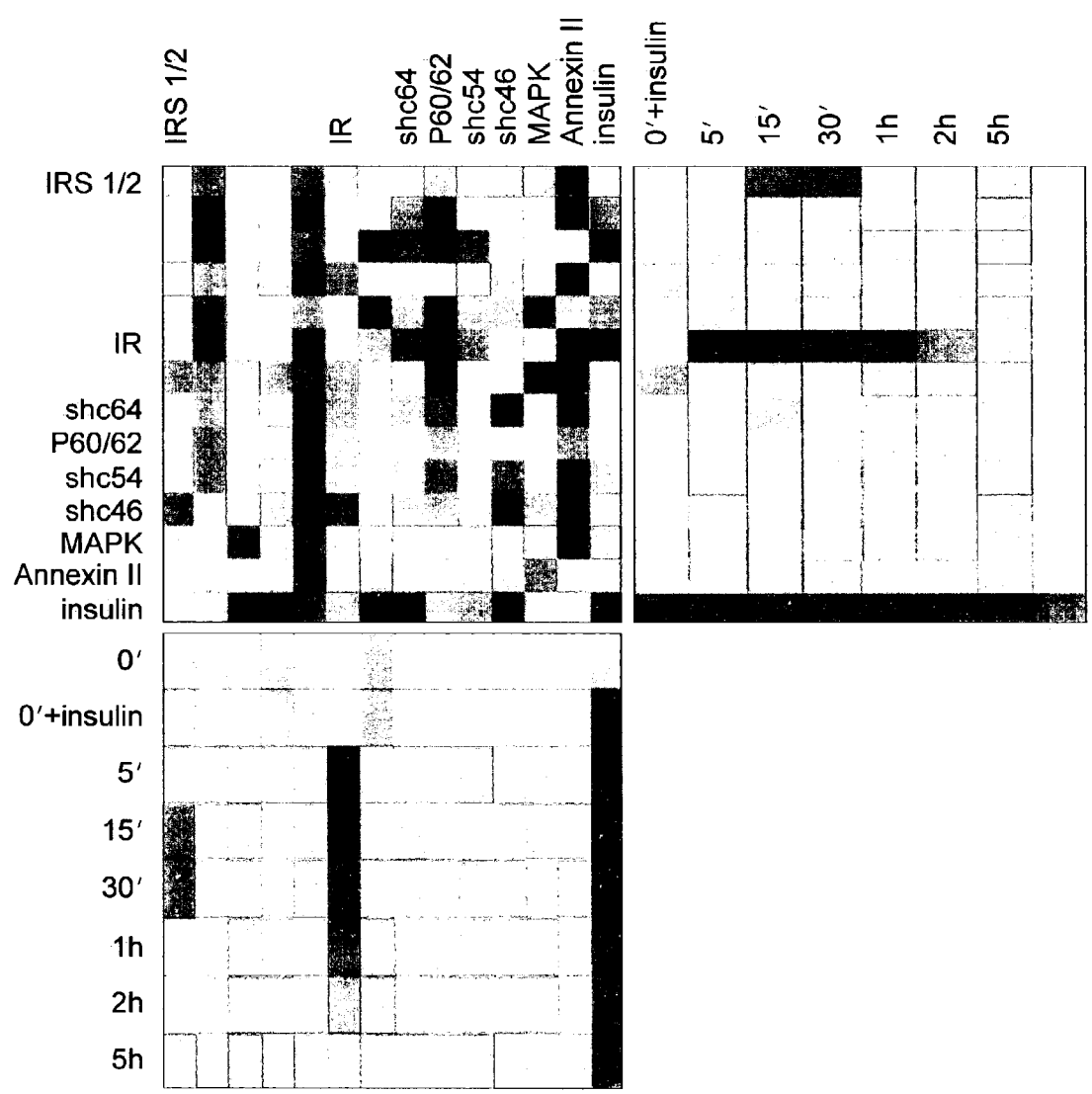
FIG. 7(A) is a color graphic depiction of the data sets and the matrix of weight parameters obtained from the neural network analysis of insulin induced time dependent phosphorylation.

The measured intensities of the phosphorylated bands averaged on four data sets and normalized to the maximal value of each band were presented to the neural network, with target outputs taken as the next time input sets. The resulted neural network matrix of weight parameters along with the data sets (corresponding to the convention of FIG. 1) are shown in FIG. 7(A). From the temporal relations between the changes of the phosphorylation levels, the analysis extracted the hierarchic information about the interactions between the components. The list of largest (positive and negative) weight parameters is given in Table 3. For clarity we omitted from the list the diagonal elements (A→A), redundant consequences (A→C if A→B and B→C are listed) as well as the unidentified bands. The list can be compiled literally as interaction strength parameters to draw the activation pathway architecture shown in FIG. 7(B). The analysis gives the strength and sign (inducing versus inhibiting) for these interactions as presented in FIG. 7(B) by arrow-heads and bar-heads, respectively. To draw the pathway we start with the stimulus, namely insulin and connect to it with a inducing interaction arrow to the molecule with the strongest weight, here IR (last in the listing of table 3).

Next we connect lines from IR to all the molecules appearing in the listing to have inducing interactions emerging from IR, here the three shc molecules, IRS1/2 and P60/62, etc. After completing the inducing interactions we fill in the inhibiting lines, FIG. 7(B) shows that the temporal analysis applied here recognizes known key features in the sequence of activated events in the insulin-activated pathway, namely the strong inter-relationship of the elevation of tyrosine phosphorylation of IR1/2, IRS, P60/62 and the three Shc proteins. In addition, FIG. 7(B) shows that the feedback contributions of Annexin II down-regulates the insulin response. Clearly normalized interaction strength parameters below about 0.2 strongly reflect errors inherent to quantitative gel measurements.

The above examples illustrate the types of applications and interpretations that simple neural networks can yield in such an environment. It should be noted in this regard that no new data has been, or need be, generated. Rather, exhaustive use of all the information available from experiments can be achieved. Data from repeated experiments and new results can be readily added to existing data sets. The invention thus improves the statistical quality of the results, and achieves results that are consistent with the widest range of available experimental data.

It should of course be observed that the activity of different enzymes and cell signaling molecules is not proportional to their tyrosine phosphorylation level, and varies drastically between molecules. In addition, cells respond to stimuli by translocation of target molecules between compartments. Following the fast responses that are probed by phosphorylation, the activity of components may be modulated by local effective concentrations and accessibility. Total cell extracts and gel analysis do not reflect these changes, and they introduce arbitrary scale factors between the measured variables and the functional activity modulating the weight parameters. This evidently reflects on the hierarchies deduced from weight parameters. Same kind of limitations apply for the analysis of gene expression by DNA chip technology.

Therefore the results achieved by the invention should not be considered as quantitative in molecular terms, even though the data themselves are. However, there are ways overcome these problems, such as by subcellular fragmentation, quantification of contraction dependencies in variable expression constructs, microscope quantification of subcellular localization using multiple fluorescence labeling, and variation of concentrations of drugs like vanadate to evaluate kinase and phosphatase activation dynamics. It is emphasized though that the purpose of the invention is not to provide precise mathematical modeling of complex biological processes, but rather to characterize behavior of measured variables that are related by a network of interactions (dependencies). It is expected that while moving from responsive cell lines with high level of expression of relevant proteins to live tissue or developing embryos, the linked behavior of these variables will be preserved, and the invention can help resolve distributed changes that reflect these linked (correlated) patterns. Such fingerprints of linked variables can be used to characterize complex cellular states such as growth arrest, proliferation, apoptosis and differentiation. DNA chips and differential display maps in transformed cell lines provide a source of data for such fingerprinting, and may demonstrate its usefulness for diagnostic purposes.

The analysis is applicable to characterize complex, multicomponent biological processes. It is of course apparent that the invention is equally applicable to other nonbiological complex multivariable systems and data sets.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

TABLE 1

EGFR-specific tyrosine phosphorylations

| Spot | M.W. | pI | $^{32}$-P EGFR | $^{32}$-P EGFR/erbB2 | $p^Y$ EGFR | $p^Y$ EGFR/erbB2 |
|---|---|---|---|---|---|---|
| 1 | 109 | 5.1–5.2 | + | − | + | − |
| 2 | 103 | 6–6.7 | ++ | + | − | − |
| 3 | 82.5 | 5.2–5.4 | +++ | − | + | − |
| 4 | 81 | 5–5.1 | + | − | − | − |
| 5 | 77 | 5.5–5.6 | + | − | − | − |
| 6 | 70 | 4.9 | ++ | − | ± | − |
| 7 | 70 | 4.9 | ++ | − | ± | − |
| 8 | 67 | 4.8 | + | − | ++ | + |
| 9 | 67 | 5–5.3 | + | − | ++ | − |
| 10 | 56 | 5.6–6.7 | +++ | ++ | ++ | + |
| 11 | 51 | 5.6–5.8 | + | − | − | − |
| 12 | 50 | 6.5–6.7 | + | − | − | − |
| 13 | 47 | 5.3 | − | − | + | − |
| 14 | 46.5 | 5.4 | − | − | + | − |
| 15 | 46 | 5.6 | − | − | + | − |
| 16 | 45 | 6.0 | − | − | + | − |
| 17 | 41 | 7.5 | +++ | + | ++ | − |
| 18 | 40 | 5.7 | + | − | − | − |
| 19 | 40 | 5.9 | ± | − | − | − |
| 20 | 40 | 7.5 | +++ | + | + | − |
| 21 | 39.5 | 7.5 | +++ | + | + | − |
| 22 | 38 | 5.9 | + | − | − | − |
| 23 | 35.5 | 5.1 | ± | − | − | − |
| 24 | 33–36 | 4.5–4.9 | ++ | − | ++* | + |
| 25 | 35 | 5.6 | ++ | + | + | − |
| 26 | 32 | 5.8 | + | − | − | − |
| 27 | 29 | 5.4 | + | ± | − | − |
| 28 | 28 | 4.9 | ++ | ± | +* | + |
| 29 | 28 | 5.8 | ++ | + | + | − |
| 30 | 25 | 5.6 | ++ | ± | − | − |
| 31 | 24 | 5.4 | ++ | ± | − | − |
| 32 | 21.5 | 6.3 | +++ | + | +++ | + |

TABLE 2 erbB-2-specific tyrosine phosphorylations

| Spot | M.W. | pI | $^{32}$-P EGFR | $^{32}$-P EGFR/erbB2 | $p^Y$ EGFR | $p^Y$ EGFR/erbB2 |
|---|---|---|---|---|---|---|
| A | 160 | 6.1–6.7 | + | +++ | − | − |
| B | 151 | 5.2–5.4 | − | − | − | +++ |
| C | 140 | 5.6–6 | + | +++ | − | − |
| D | 130 | 6.1–6.7 | + | +++ | ± | + |
| E | 97 | 5.1 | − | ++ | − | − |
| F | 92 | 5.1 | − | ++ | − | − |
| G | 80 | 5.7–5.9 | − | ++ | − | + |
| H | 72 | 5.1–5.3 | + | ++ | + | +++ |
| I | 74 | 6.4–6.8 | + | ++ | − | + |
| J | 68 | 5.3–5.5 | + | ++ | + | +++ |
| K | 58 | 4.7 | + | ++ | ++ | +++ |
| L | 56 | 5.2 | + | ++ | − | + |
| M | 53 | 5.3–5.4 | + | +++ | − | − |
| N | 41 | 6 | ± | + | ± | + |
| O | 40 | 6.5 | − | + | − | − |
| P | 39 | 4.8–5 | ± | + | − | + |
| Q | 38 | 5.6–6 | − | ± | − | − |
| R | 37.5 | 5 | − | + | − | + |

TABLE 2-continued erbB-2-specific tyrosine phosphorylations

| | | | $^{32}$-P | | $p^Y$ | |
|---|---|---|---|---|---|---|
| Spot | M.W. | pI | EGFR | EGFR/erbB2 | EGFR | EGFR/erbB2 |
| S | 36 | 5.1 | + | ++ | ± | ++ |
| T | 35.5 | 5.2 | + | ++ | − | + |
| U | 34 | 5.8 | − | + | − | − |
| V | 33 | 5.1 | − | + | − | − |
| W | 33 | 5.3 | − | ± | − | + |
| X | 25 | 6.3 | − | + | − | + |
| Y | 31.5 | 6.1 | − | ± | − | ++ |
| Z | 23.5 | 6.3 | + | +++ | + | +++ |
| alpha | 22.5 | 4.5 | − | + | − | − |
| beta | 20 | 4.6 | − | + | − | − |

TABLE 3

WEIGHT PARAMETERS HIERARCHICAL LISTING

```
Neuron Max W(j,i) [j,i] for largest Neg elements
Annexin -> MAPK   W[ 12, 13]= −0.4513958E+00 −0.5684727E+00
Annexin -> IRS 1/2 W[ 1, 13]= −0.3786016E+00 −0.4767981E+00
Annexin -> shc46  W[ 11, 13]= −0.2825637E+00 −0.3558512E+00
Annexin -> IR     W[ 6, 13]= −0.2200239E+00 −0.2770907E+00
shc46 -> Insulin  W[ 14, 11]= −0.1523805E+00 −0.1919028E+00
Annexin -> shc64  W[ 8, 13]= −0.1471602E+00 −0.1853286E+00
p60/62 -> IR      W[ 6, 9]= −0.1409255E+00 −0.1774769E+00
shc64 -> Insulin  W[ 14, 8]= −0.1241601E+00 −0.1563631E+00
IRS 1/2 -> shc46  W[ 11, 1]= −0.1171511E+00 −0.1475362E+00
NeuronMax W(j,i) [j,i] for largest Pos elements
IRS 1/2 -> IR     W[ 6, 1]= 0.2283042E+00 0.2875187E+00
IRS 1/2 -> MAPK   W[ 12, 1]= 0.2706531E+00 0.3408515E+00
IRS 1/2 -> Annexin W[ 13, 1]= 0.2834824E+00 0.3570082E+00
shc46 -> MAPK     W[ 12, 11]= 0.3015976E+00 0.3798219E+00
IRS 1/2 -> Insulin W[ 14, 1]= 0.3411053E+00 0.4295765E+00
IR -> shc54       W[ 10, 6]= 0.4214110E+00 0.5307109E+00
IR -> IRS 1/2     W[ 1, 6]= 0.4228618E+00 0.5325379E+00
IR -> p60/62      W[ 9, 6]= 0.4237712E+00 0.5336832E+00
IR -> shc64       W[ 8, 6]= 0.4655531E+00 0.5863019E+00
MAPK -> Annexin   W[ 13, 12]= 0.5381577E+00 0.6777377E+00
IR -> shc46       W[ 11, 6]= 0.5831921E+00 0.7344525E+00
Insulin -> IR     W[ 6, 14]= 0.7648531E+00 0.9632303E+00
```

LIST OF ALPHABETIC REFERENCES

Alberts et al, Part III: "Internal Organization of the Cell" Ch. 15: "Cell Signaling", in: "Molecular biology of the cell", Garland Publishing, New York. 3$^{rd}$ edition (1994).

Beale, R. and Jackson, T., "Neural computing: An introduction," Adam Hilger NY 1990).

Biener, Y., Feinstein, R., Mayak, M., Kaburagi, Y., Kadowaki, T. and Zick, Y. "Annexin II is a novel player in insulin signal transduction." J. Biol. Chem. 271:29489–29496 (1996).

Bray, D., Bourret, R. B. and Simon, M. I. "Computer simulation of the phosphorylation cascade controlling bacterial chemotaxis" Mol. Biol. Of the Cell 4:469–482 (1993).

Bray, "Intracellular signaling as a Parallel Distributed Process" J. Theor. Biol. 143:215–231 (1990).

Burstein, "A network model of developmental genes hierarchy." J. Theor. Biol. 174:1–11 (1995).

Chock, P. B. and Stadtman, E. R. "Superiority of interconvertible enzyme cascades in metabolic regulation: analysis of multicyclic systems." Proc. Natl. Acad. Sci. USA 74:2766–2770 (1977).

Demuth, H. and Beale, M. MATLAB Neural Network TOOLBOX, The MATH WORKS Inc., Natick Mass. (1993).

Fearon, E. R. and Vogelstein, B. "A genetic model for colorectal tumorigenesis." Cell 61:759–767 (1990).

Hjelmfelt, A., Schneider, F. A. and Ross, J. "Pattern recognition in coupled chemical kinetic systems." Science 260:335–337 (1993).

Press, W. H., Teukolsky, S. A., Vetterling, W. T. & Plannery, B. P. (1992) Numerical Reciepts 2$^{nd}$ edition Cambridge Univ. Press.

Prigent, S, A. and Gullick, W. J. "Identification of c-erbB-3 binding sites for phosphatidylinositol 3'-kinase and SHC using an EGF receptor/c-34bB-3 3 chimera." EMBO J. 13:2831–2841 (1994).

Romano, A., Wong, W. T., Santoro, M., Wirth, P. J., Thorgeirsson, S. S. and Di Fiore, P. P. "The high transforming potency of erbB-2 and ret is associated with phosphorylation of Paxillin and a 23 Kda protein." Oncogene 9:2923–2933 (1994).

What is claimed is:

1. Apparatus for analyzing a biological system defined by multivariable data sets including a plurality of perturbations (inputs) and measured response (outputs) variables, said apparatus comprising:

a neural network capable of receiving signals contained in said data sets and processing said inputs according to an artificial intelligence program to yield the outputs; and means for obtaining a trained matrix of weight parameters for said neural network and said data sets through a sequence of iterations, starting at random guess for the weights, and correcting the trained weight matrix according to a learning rule until the errors between the processed inputs and the outputs diminishes;

means for obtaining an average matrix of weight parameters of many trained weight matrices including sequentially and repeatedly averaging said many trained weight matrices, each initialized by a different set of a plurality of random weight parameters, and until the averaged matrix of weight parameters converge;

means of evaluation of the relationship between said variables from said weight parameters; and means for collecting data sets which include a plurality of induced and measured variables which characterize stimuli applied to cells and responses of said cells to said stimuli, wherein said weight parameters of the neural network provide identification of finger prints of complex cellular states, wherein said data sets comprise experimentally determined data which characterize variations in measurable components of a biological process.

2. Apparatus according to claim 1 wherein said external stimuluss selected from the group consisting of a drug, growth factor, hormone, a mutated proteins and forced expression or suppression of cellular component, and said complex cellular state is starvation, appoptosis, cell differentiation, mitogenicity of proliferating cells or cell cycle arrest.

3. Apparatus according to claim 1 for construction of hierarchical architecture of interaction network between said components of said biological process by analysis of cell responses to external stimuli, comprising:

means for collecting time dependent data sets which includes a plurality of changing variables which characterize responses of said cells to said stimuli, wherein said weight parameters allow the construction of hierarchical architecture of said interaction network.

4. Apparatus according to claim 3 wherein said network is a signaling pathway in cells.

5. Apparatus according to claim 1 wherein said neural network matrix of weight parameters is represented by a color coded image, in which dominating positive and negative weight parameters are easily identified.

6. Apparatus according to claim 1 wherein said matrix of weight parameters $W_{ji}$ operates on input variables $I(k)_j$, though a monotonic transfer function to generate output variables $O(k)_i$, according to:

$$O(k)_j = f\left\{\sum_{i=1,N} W_{ji} * I(k)_j + B_j\right\} (k = 1, L; j = 1, M). \quad \text{(Eq. 1)}$$

7. Process for analyzing a biological system defined by multivariable data sets including a plurality of perturbations and measured response variables, said process comprising:
providing a neural network;
applying signals representative of variables contained in said data sets to said neural network and through a sequence of iterations, starting at a random guess for trained weight parameters, and correcting the trained weight parameters according to a learning rule until the error between the signal and the responses diminishes, and repeatedly averaging a plurality of trained weight parameters each initialized by a different random guess for the trained weight parameters, until an average of the plurality of trained weight parameters converge; and
generating from the average trained weight parameters an evaluation, indicating relationship between said variables,
wherein said matrix of weight parameters $W_{ji}$ operates on input variables $I(k)_j$, through a monotonic transfer function to generate output variables $O(k)_j$, according to:

$$O(k)_i = f\left\{\sum_{i=1,N} W_{ji} * I(k)_j + B_j\right\} (k = 1, L; j = 1, M) \quad \text{(Eq. 1)}$$

to provide identification of finger prints of complex cellular states.

8. Method comprising the steps of
obtaining a data set comprising a plurality of input/output multivariable vectors representative of a biological process involving many interacting multifunctional components in at least one pathway,
establishing a neural network comprised of single layer network operators, applying the data set to the neural network, and
training the neural network by a training algorithm to implement a transformation by a matrix of weights, including sequentially initializing a plurality of weight matrices, wherein each of the weight matrices is initialized with a different random guess and iteratively correcting each of the weight matrices until the processed inputs and outputs are within a small error for each of the weight matrices, yielding a plurality of trained weight matrices, of the plurality of trained weight matrices to form the matrix of weights, till convergence to the process of averaging together the plurality of trained weight matrices, determining from said matrix of weights the hierarchical structure between said components,
wherein the hierarchical structure is portrayed by drawing the vectors between the variables as determined by the magnitude of the matrix of weights, and
wherein weights smaller than a preselected threshold are ignored in the portrayal providing for distinct neural network identification of finger prints of complex cellular states.

9. The method of claim 8 wherein the data set of input/output multivariable vectors constitutes time dependent data.

10. The method of claim 9 wherein the data set includes an input set including a measured set of variables at consecutive times, and an output set comprised of the same data as the input set, but shifted forward in time to a later time, so that the neural network learns to take in data at one time and give out data at the later time.

11. Method comprising the steps of
obtaining a data set comprising a plurality of input multivariable vectors representative of a biological system involving many interacting multifunctional components in at least one pathway, that define a complex biological state,
determining a corresponding output vector for each input vector that defines classes for the input vectors,
establishing a neural network comprised of single layer network operators, applying the data set to the neural network,
training the neural network by a training algorithm to implement a transformation by a matrix of weights, including sequentially initializing a plurality of weight matrices, wherein each of the weight matrices is initialized with a random guess and iteratively modified according to a learning rule until the transformation of inputs by the weight matrix gives the outputs,
averaging the trained solutions for the plurality of weight matrices to obtain a converged averaged weight matrix, whereby the modified neural network can sort newly presented input vectors into the classes that were defined by the output set of vectors in the training to provide classification of finger prints of complex cellular states.

12. Apparatus for processing input vectors representative of a biological process involving many interacting multifunctional components in at least one pathway comprising,
a neural network composed of single layer network operators trained by a training algorithm to implement a transformation by a matrix of weights, the training including sequentially initializing a plurality of weight matrices, wherein each of the weight matrices is initialized with a random guess and iteratively modified according to a learning rule until the weight matrix produces a solution that transforms the inputs to the outputs within a small error, and then averaging the trained solutions of the weight matrices, each obtained from a different plurality of initial weights to obtain a converged averaged weight matrix, and
a device for recognizing a predetermined input vector based on the output vectors received by the mechanism,
wherein the input vectors are sorted according to predetermined criteria for the output vectors to provide classification of finger prints of complex cellular states.

* * * * *